(12) United States Patent
Wilson et al.

(10) Patent No.: US 7,629,379 B2
(45) Date of Patent: Dec. 8, 2009

(54) SUBSTITUTED PHOSPHONATE FLUORESCENT SENSORS AND USE THEREOF

(75) Inventors: John Robert Howe Wilson, London (GB); Alice Caroline Sullivan, London (GB); Siud Pui Man, London (GB); Lesley Robson, London (GB)

(73) Assignee: Queen Mary & Westfield College, London (GB)

( * ) Notice: Subject to any disclaimer, the term of this patent is extended or adjusted under 35 U.S.C. 154(b) by 356 days.

(21) Appl. No.: 10/557,073

(22) PCT Filed: May 14, 2004

(86) PCT No.: PCT/GB2004/002084
§ 371 (c)(1),
(2), (4) Date: Nov. 21, 2006

(87) PCT Pub. No.: WO2004/101579
PCT Pub. Date: Nov. 25, 2004

(65) Prior Publication Data
US 2007/0049761 A1 Mar. 1, 2007

(30) Foreign Application Priority Data
May 17, 2003 (GB) ................... 0311406.3

(51) Int. Cl.
*A61K 31/35* (2006.01)
*C07F 9/28* (2006.01)
(52) U.S. Cl. .................. 514/456; 548/439; 548/509; 548/146; 546/339; 549/218
(58) Field of Classification Search ................ 548/439, 548/509, 146; 546/339; 549/218; 514/456
See application file for complete search history.

(56) References Cited
U.S. PATENT DOCUMENTS
5,453,517 A 9/1995 Kuhn et al.

FOREIGN PATENT DOCUMENTS
WO WO 99/58521 11/1999
WO WO 01/51497 7/2001
WO WO 02/38190 5/2002

OTHER PUBLICATIONS

Tanaka et al., 1990, CAS: 112:108695.*
Arimilli et al., 2003, CAS: 139:381609.*
Erion et al., 2000, CAS: 133:84284.*
Dang et al., 2000, CAS: 132:222529.*
Van Poelje et al., 2002, CAS: 136:123595.*
Erion et al., 2001, CAS: 135:348869.*
Kasibhatla et al., 1998, CAS: 129: 245147.*
He et al., 1993, CAS: 119:203497.*

Bartsch et al., "Selective transport of alkali metal cations in solvent extraction by proton-ionizable dibenzocrown ethers," Database Caplus, Chemical Abstracts Service, XP002310237 (1p.).
He et al., "Study on organophosphorus compounds with biological activity. Part III. Synthesis properties and biological activity of .alpha.-(benzothiazol-2-yl-oxy)alkanephosphonates," Database Caplus, Chemical Abstracts Service, XP002310235 (1p).
Jurecka et al., "Synthesis, characterization and extraction behaviour of calyx'4!arene-based phosphonic acids," *J of the Chemical Society* (2002) pp. 1370-1377.

(Continued)

*Primary Examiner*—Rei-tsang Shiao
(74) *Attorney, Agent, or Firm*—Pepper Hamilton LLP

(57) ABSTRACT

The invention relates to new compounds of formula (1) wherein R is hydrogen or a linear or branched $C_{1-40}$ alkyl; where X is O, S, or $NR^1$ where $R^1$ is a hydrogen, a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group and where one or both of C and D is $OR^2$, $SR^2$, $NR^3R^4$ where $R^2$, $R^3$ and $R^4$ are each independently hydrogen, a linear or branched $C_{1-40}$ alkyl, $C_{2-40}$ alkenyl or $C_{2-40}$ alkynyl group, an aryl or $C_{1-40}$ alkylaryl group or a linear or branched $C_{1-40}$ alkyl $NR^5R^6$ chain where $R^5$ and $R^6$ are each independently hydrogen, a linear or branched $C_{1-40}$ alkyl; or an optionally complex metal ion $M^{n+}/n$ wherein n is an integer from 1 to 8; or where one or both of C and D are amino acids or nucleic acids attached via either N, O or S; and wherein m is an integer from 1 to 8; and wherein either: I) A is a known aryl or heteroaryl fluorescent group and B is hydrogen, a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group or phosphonate $P(O)(OR^2)_2$; II) B is a known aryl or heteroaryl fluorescent group and A is hydrogen, a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group or a linear or branched $C_{1-40}$ alkyl $NR^5R^6$ chain, or a linear or branched $C_{1-40\ alkyl}$ mono or di ester $C_{1-40}$ alkylphosphonate or a linear or branched $C_{1-40}$ alkylphosphonic acid; III) Both A and B are known aryl or heteroaryl fluorescent groups. The compounds are useful as fluorescent sensors for metal cations and have the advantages of excellent water solubility, selectivity and sensitivity to a variety of metal cations even in the presence of high concentrations of $Ca^{+2}$ $Na^+$ and $K^+$, good cell permeability, flexible and simple syntheses, ease of attachment to polymers and bio-polymers to aid the identification of both chemical and biological processes as well as for assaying physiological samples and for the attachment to surfaces such as glasses, ceramics and apatites.

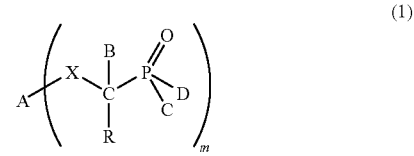

(1)

7 Claims, No Drawings

OTHER PUBLICATIONS

Komlev et al., "Phosphorylation of some organic luminophors," Database Caplus, Chemical Abstracts Service, XP002310236 (1p).

Kunsagi-Mate et al., "Complex formation between 1-chloro-4-(trifluoromethyl)benzene (guest) and 4-*tert*-butylcalix[4]arenes (host) distally substituted with phosphoric acid or phosphonic ester groups at the lower rim," *Tetrahedron* (2002) 58(25):5119-5124.

Pugia et al., "Effect of sidearm length upon competitive alkali metal solvent extraction into chloroform by lipophilic crown phosphonic acid monoalkyl esters," *Analytical Chemistry* (1986) 58(13):2723-2726.

Sorori et al., "Lithographic printing plate master for CTP (computer-to-plate) platemaking," Database Caplus, Chemical Abstracts Service, XP002310234 (1p).

* cited by examiner

SUBSTITUTED PHOSPHONATE FLUORESCENT SENSORS AND USE THEREOF

CROSS-REFERENCE TO RELATED APPLICATIONS

This application is the U.S. National Stage filing of International Application Ser. No. PCT/GB2004/002084 filed May 14, 2004, which claims priority to GB 0311406.3 filed May 17, 2003, each of which is incorporated herein by reference in its entirety.

The invention relates a family of novel substituted fluorescent phosphonate derivatives that are useful for the detection, discrimination and quantification of metal cations in various environments including aqueous and biological media as well as for the identification of biological processes and the assaying of physiological samples.

Metal ions are found throughout nature and the environment and are essential components of all biological systems. Cells use metal cations to perform a wide variety of functions. For example metal cations are involved in a large number of enzyme catalysed reactions, as well as messengers, gas carriers, templates for bio-polymer formation such as DNA, immune system function and regulatory elements for gene transcription. Metals such as divalent zinc ($Zn^{+2}$) play an essential role in biology and nutrition. Minor perturbations of the metal ion concentrations can lead to a host of different diseases. For example changes in $Zn^{+2}$ levels have been linked with retarded sexual maturation, Alzheimer's disease, stunted growth and skin damage. The brain contains large amounts of chelatable $Zn^{+2}$, present mainly in vesicles within excitatory nerve terminals. $Zn^{+2}$ regulates the function of certain postsynaptic receptors and is a contributing factor in a number of neurological disorders. $Zn^{+2}$ also plays an important role as a nutrient in oceans and is required at nano level concentrations.

Metal cations are also used in a very large number of chemical processes as well as a host of other industrial applications. As a consequence these metal cations are found throughout the environment and are a major source of contamination. Some of the most toxic metal ions in environmental samples are those that are readily soluble in water. Current detection methods for soluble metal cations involve the use of instrumentation that is not readily transportable in the field. Also experimental difficulties and inaccuracies are encountered if measurements are delayed. Simple hand held analytical equipment would be of significant benefit. An attractive potential option would be fluorescent reagents that can simply and cheaply detect a variety of metal ions and can also differentiate between different metal ions as well as oxidation states in a wide range of environmental and industrial solutions. Of particular importance is the ability to detect such metal ions in aqueous environments as well as in typical biological fluids.

Current fluorescent sensors contain a metal chelator, primarily carboxy, sulfonic acids and their salts, and amines, covalently attached to a fluorophore. Examples of chelators include heteroaromatic nitrogen atoms—U.S. Pat. Nos. 6,013,802, 5,928,955 and Chem. Commun., 2002, 1424-5— carboxylate anions—U.S. Pat. No. 4,603,209, U.S. Pat. No. 5,049,673, U.S. Pat. No. 4,849,362, U.S. Pat. No. 5,453,517, U.S. Pat. No. 5,501,980 and U.S. Pat. No. 5,459,276— and cyclic polyethers—U.S. Pat. No. 5,134,232 and U.S. Pat. No. 5,405,975. Other examples can be found in Practical Fluorescence, $2^{nd}$ edition, Publisher Marcel Dekker 1990. Previously known carboxylate fluorescent metal ion chelators usually suffer from high sensitivity to micromolar concentrations of $Ca^{+2}$ ions or millimolar concentrations of $Na^+$ or $K^+$. This is a serious imitation when the requirement is to detect extremely small concentrations of metal ions in the presence of other metal ions in biological fluids, seawater or waste stream or waters. Many of the above reagents, due to their lack of water solubility, require first extraction of the metal into an organic solvent prior to its detection or quantification. This is a serious limitation and water-soluble fluorescent sensors are the preferred option. Furthermore many of the above examples result, on metal detection, in a reduction in fluorescence intensity rather than the experimentally preferred enhancement. Another class of sensors, recently reported—J. Am. Chem. Soc., 2000, 122, 5644 and 12399 and Angew. Chem., Int. Ed 2000, 39, 1052—include the aliphatic tertiary amine functionality as chelator. At physiological pH these groups are significantly protonated thus limiting their applicability as metal sensors.

The current technologies for detecting free $Zn^{+2}$ have sensitivities in the micro to nano molar level. These include substituted quinolines, or compounds containing the dansyl group—Chem Commun., 2002, 1425-6 and U.S. Pat. No. 5,928,955. Reported limitations here include low sensitivity, lack of specificity in the presence of other transition metal cations, low membrane permeability, limited water solubility and complex and costly syntheses.

The present invention relates to novel compounds which are capable of acting as fluorescent sensors, or which are precursors for these, for the detection, discrimination and quantification of metal cations in a wide range of solvents including aqueous and biological media as well as for the identification of biological processes and the assaying of physiological samples. Therefore, in a first aspect of the present invention, there is provided a compound of General Formula 1:

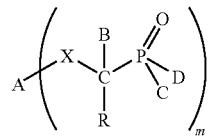

Formula 1 wherein R is hydrogen or a linear or branched $C_{1-40}$ alkyl; where X is O, S, or $NR^1$ where $R^1$ is a hydrogen, a linear or branched $C_{1-40}$ alkyl, $C_{2-40}$ alkenyl or $C_{2-40}$ alkynyl group, an aryl, a heteroaryl or $C_{1-40}$alkylaryl or alkylheteroaryl group and where one or both of C and D is $OR^2$, $SR^2$, $NR^3R^4$ where $R^2$, $R^3$, and $R^4$ are each independently hydrogen, a linear or branched $C_{1-40}$ alkyl, $C_{2-40}$ alkenyl or $C_{2-40}$ alkynyl group, an aryl or $C_{1-40}$ alkylaryl group, or an optionally complex metal ion $M^{n+}/n$ wherein n is an integer from 1 to 8, or a linear or branched $C_{1-40}$ alkyl $NR^5R^6$ chain $NR^5R^6$ terminated alkyl chain where $R^5$ and $R^6$ are each independently hydrogen, a linear or branched $C_{1-40}$ alkyl; or where one or both of C and D are amino acids or nucleic acids attached via either N, O or S; and wherein m is an integer from 1 to 8; and wherein either.

I) A is a known aryl or heteroaryl fluorescent group and B is hydrogen, a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group or phosphonate $P(O)(OR^2)_2$;

II) B is a known aryl or heteroaryl fluorescent group and A is hydrogen, a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group or a linear or branched $C_{1-40}$ alkyl $NR^5R^6$ chain, or a linear or branched $C_{1-40}$ mono or di akyl ester $C_{1-40}$ alkylphosphonate or a linear or branched $C_{1-40}$ alkylphosphonic acid;

III) Both A and B are known aryl or heteroaryl fluorescent groups.

Advantage of these new fluorescent sensors include excellent water solubility, selectivity and sensitivity to a variety of metal cations even in the presence of high concentrations of $Ca^{+2}$, $Na^+$ and $K^+$ and a range of compounds typically found in various biological media, good cell permeability, flexible and simple syntheses, ease of attachment to polymers and bio-polymers to aid the identification of both chemical and biological processes as well as for assaying physiological samples and for the attachment to surfaces such as glasses, ceramics and apatites.

In the context of the present invention known fluorophores include but are not limited to xanthenes, fluoresceins, benzofluoroescins, naphthofluorescins, eosins, erytbrosins, rosamines, rhodamines, sulforhodamines, rhodols, benzimidazoles, phenoxazines, resorufin, ethidiums, propidiums, anthracyclines, mithramycins, acridines, actinomycins, styryl dyes, carbocyanines, merocyanines, coumarins, pyrenes, cyrysenes, stilbenes, carbazines, carbazoles, porphyrins, metal complexed porphyrins, anthracenes, naphthalenes, quinolines, indoles, pynidines, bipyridyls, phenanthrolines, dansyl, salicyclic acids, anthranlic acids, benz-2-oxa-1,3-diazoles, tyrosine and fluorescamine. Included also are substituted variants and metal complexes of the above.

In the context of the present invention, $C_{1-40}$ alkyl refers to a straight, branched or cyclic hydrocarbon chain having from one to forty carbon atoms. The $C_{1-40}$ alkyl group may be substituted with one or more substituents selected from nitro, chloro, fluoro, bromo, nitrile, sulfonic acid or salt of sulfonic acid, carboxy, carboxyalkyl, carboxyalkoxy, carboxylalkylamino, carboxyalkylthio, $C_{1-6}$ alkoxy, di $C_{1-40}$ alkyl phosphonate, $C_{1-40}$ alkyl phosphonate, phosphonic acid, amino, amino $C_{1-40}$ alkyl or amino di ($C_{1-40}$ alkyl). Examples include methyl, ethyl, isopropyl, n-propyl, butyl, tert-butyl, n-hexyl, n-decyl, n-dodecyl, cyclohexyl, octyl, iso-octyl, hexadecyl, octadecyl, iso-octadecyl and docosyl. A $C_{1-12}$-alkyl group has from one to twelve carbon atoms.

In the context of the present invention, $C_{2-40}$ alkenyl refers to a straight, branched or cyclic hydrocarbon chain having from one to forty carbon atoms and including at least one carbon-arbon double bond. The $C_{2-40}$ alkenyl group may be substituted with one or more substituents selected from nitro, chloro, fluoro, bromo, nitrile, sulfonic acid or salt of sulfonic acid, carboxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di ($C_{1-40}$-alkyl). Examples include ethenyl, 2-propenyl, cyclohexenyl, octenyl, iso-octenyl, hexadecenyl, octadecenyl, iso-octadecenyl and docosenyl.

In the context of the present invention, $C_{2-40}$ alkynyl refers to a straight, branched or cyclic hydrocarbon chain having from one to forty carbon atoms and including at least one carbon-carbon triple bond. The $C_{2-40}$ alkynyl group may be substituted with one or more substituents selected from nitro, chloro, fluoro, bromo, nitrile, sulfonic acid or salt of sulfonic acid, carboxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di ($C_{1-40}$-alkyl). Examples include ethynyl, 2-propynyl octynyl, iso-octynyl, hexadecynyl, octadecynyl, iso-octadecynyl and docosynyl.

$C_{1-6}$ alkoxy refers to a straight or branched hydrocarbon chain having from one to six carbon atoms and attached to an oxygen atom. Examples include methoxy, ethoxy, propoxy, tert-butoxy and n-butoxy.

The term aryl refers to a five or six membered cyclic, 8-10 membered bicyclic or 10-14 membered tricyclic group or up to a 10 fused ringed polyaromatic system with aromatic character and includes systems which contain one or more heteroatoms, for example, N, O or S. The aryl group may be substituted with one or more substituents selected from nitro, chloro, fluoro, bromo, nitrile, sulfonic acid or salt of sulfonic acid, carboxy, carboxyalicyl, carboxyalkoxy, carboxylalkylamino, carboxyalkylthio, $C_{1-6}$ alkoxy, di $C_{1-40}$ alkyl phosphonate, $C_{1-40}$ alkyl phosphonate, phosphonic acid, amino, amino $C_{1-40}$-alkyl or amino di ($C_{1-40}$-alkyl).

Heteroaryl, as used herein, is an aromatic group that contains at least one heteroatom (a non-carbon atom forming the ring structure) and is optionally a single, two, three, four, five, six ringed structure or a fused 2-, 3-, 4-, 5-, 6-, 7- or 8-ring structure. Examples include pyrrolyl, pyridyl, thienyl, furanyl, oxazolyl, isoazolyl, oxadiazolyl, imidazolyl, benzoxazolyl, benzothiazolyl, benzimidazolyl, quinolyl, benzofuranyl, indolyl, carbazolyl, coumarins and benzocoumarins. The heteroaryl group may be substituted with one or more substituents selected from nitro, chloro, fluoro, bromo, nitriue, sulfonic acid or salt of sulfonic acid, carboxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, ammo, amino $C_{1-40}$-alkyl or amino di ($C_{1-40}$-alkyl). Such substituents are typically used to modify the spectral properties, affinity, selectivity, solubility or any combination of these factors.

The term $C_{1-40}$ alkylaryl group refers to a straight or branched hydrocarbon chain having from one to forty carbon atoms linked to an aryl group. The $C_{1-40}$ alkylaryl group may be substituted with one or more substituents selected from nitro, chloro, fluoro, bromo, nitrile, sulfonic acid or salt of sulfonic acid, carboxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$-alkyl or amino di ($C_{1-40}$-alkyl). Examples include benzyl, phenylethyl and pyridylmethyl. In a $C_{1-8}$ alkylaryl group, the alkyl chain has from one to eight carbon atoms.

Compounds in which R and B are each independently hydrogen, X is either oxygen or nitrogen, A is a known aryl or heteroaryl fluorophore and C and D are $OR^2$ where $R^2$ is hydrogen, a $C_{1-6}$ alkyl or an optionally complex metal ion $M^{n+}/n$ wherein n is an integer from 1 to 8; and compounds in which R is hydrogen, X is either oxygen or nitrogen, A is a alkyaryl group, B is a known aryl or beteroaryl fluorophore and C and D are $OR^7$ where $R^2$ is hydrogen, a $C_{1-6}$ alkyl or an optionally complex metal ion $M^{n+}/n$ wherein n is an integer from 1 to 8; are especially preferred.

Compounds in which R is hydrogen, X is either oxygen or nitrogen, A is a alkyaryl group substituted with halogen, $C_{1-6}$ alkoxy, $C_{1-6}$ alky, hydroxyl or di alkyl phosphonate or phosphonic acid, B is a known aryl or heteroaryl fluorophore and C and D are $OR^2$ where $R^2$ is hydrogen, a $C_{1-6}$alkyl or an optionally complex metal ion $M^{n+}/n$ wherein n is an integer from 1 to 8; are especially preferred.

Compounds in which R and B are each independendy hydrogen, X is either oxygen or nitrogen attached to either the 2, 3 or 4 position of a phenyl ring which itself is attached to the 5, 10, 15 and 25 positions of a porphyrin ring, and C and D are $OR^2$ where $R^2$ is hydrogen, a $C_{1-6}$ alkyl or an optionally complex metal ion M$^{n+}$/n wherein n is an integer from 1 to 8, and m is an integer from 1 to 4 are especially preferred.

In the context of the present invention M$^{n+}$ are ions derived from lanthanide, actinide, main group (including Si and B) or transition metals and preferred M$^{n+}$ ions are derived from lanthanide, main group or transition metals.

The benefit of the compounds of Formula 1 of the present invention is further enhanced by their attachment to a variety of materials, polymers and bio-molecules. Conjugation of compounds of Formula 1 to a polymeric material or bia-molecule can be used to impart ion-sensing properties on that substance. Typical examples of such polymers and bio-molecules include, but are not limited to, antibodies, amino acids, proteins, peptides, polypeptides, bone, enzymes, enzyme substrates, lipids, phospholipids, hormones, lymphokines, metabolites, antigens, haptens, drugs, lectins, avidin, streptavidin, toxins, poisons, environmental pollutants, carbohydrates, oligosaccharides, polysaccharides, glycoproteins, glycolipids, hydroxy apatite, nucleotides, oligonucleotides, nucleic acids, and derived nucleic acids, DNA and RNA fragments and derived fragments, natural and synthetic drugs, receptors, virus particles, bacterial particles, virus components, biological cells, cellular components, natural and synthetic vesicles, polymers, polymer particles, polymer membranes, conducting and non-conducting metals and non-metals and glass, plastic surfaces, particles and optical fibres, and nanoparticles.

The desired fluorescent Formula 1-conjugate can be prepared using standard coupling reactions well known to organic and protein chemists involving the attachment of the fluorescent phosphonate group to a hydroxyl, thio or amino group of the polymer or bio-molecule. Typical reagents include, but are not limited to acid chlorides and carbodiimides. 4-Methyl-7-oxymethylphosphonic acid coumarin was attached to the nucleic acid adenosine using dicyclohexyl carbodiinide in DMF. For peptide examples see M. Bodansky, Principles of Peptide Synthesis, Springer-Verlag, Berlin 1984 and Stewart and Young, Solid Phase Peptide Synthesis, Pierce, Rockford Ill., 1984.

Compounds of Formula 1 are useful for the detection and/or quantification of metal ions, when the binding of the metal ion to the indicator, either compounds of Formula 1 or Formula 1-conjugates, results in a detectable fluorescence response. A detectable fluorescence response, as used herein, is a change in a fluorescence property of the fluorophore that is capable of being perceived, either by direct visual observation or by using an instrment, and the presence or magnitude of which is a function of the presence of the metal ion. This change, either an increase or a decrease, in a fluorescence property is a change in fluorescence quantum yield, fluorescence polarisation, fluorescence lifetime, a shift in excitation or emission wavelength or a combination of these effects. However, spectral changes that result in an enhancement of fluorescence intensity and/or a shift in the wavelength of fluorescence emission or excitation are preferred. The change in fluorescence on ion binding is variously due to conformational or electronic changes in the metal ion binding chelator that may occur in either the excited or ground state of the fluorophore, to changes in electron density at the binding site, to quenching of fluorescence by the bound metal ion or to any combination of these or other effects. The response of an individual fluorophore to a specific metal ion is dependent on the properties of both the bound and unbound fluorophore, the relative electron densities of the fluorophore and metal binding site and the ability of metal ions to quench fluorescence emission when in close proximity to a fluorophore. Selected embodiments of the invention include cases where, the fluorophore is highly fluorescent in the absence of metal ions and shows a decrease in fluorescence and fluorescence lifetime upon binding; the fluorophore is non-fluorescent or has low fluorescence and exhibits an increase in fluorescence intensity or fluorescence lifetime upon metal ion binding; the fluorescence intensity remains approximately the same but there is a shift in the excitation or emission spectrum, or both, upon metal binding.

Compounds of Formula 1 can be prepared by a number of synthetic routes. Compounds where A is a known aryl or heteroaryl fluorescent group were prepared by a variation of the methodology described in J. Chem. Soc. Perkin Trans. 1. 1994, 1897. This method is particularly appropriate given that most fluorophores contain, or can be easily substituted with, functional groups such as OH, SH or NH to which a methylene or substituted methylene phosphonate group can be attached. The methodology involves first the formation of an anion using a base followed by displacement of a leaving group from a dialkyl (Z) methylene phosphonate, where Z represents a suitable leaving group. A wide range of bases and solvents, well known to those skilled in the art of organic chemistry, can be used to conduct this reaction. Sodium hydride and sodium amide are the preferred bases. The preferred solvents are dimethyl sulfoxide and N. N dimethyl formamide. Suitable leaving groups, Z, include but not limited to halides, perchlorates, substituted alkyl and aryl sulfonates, and fluorosulfonates, with 4-chlorophenyl sulfonate and triflates especially preferred. Reaction times of between 15 minutes to 48 hours have been used and depend on the reactivity of the anion. Standard methodologies, well known to those skilled in the art of synthetic chemistry, are used to follow the reaction to completion. The synthesis of the aryl or heteroaryl starting materials is extensively described in the chemical literature.

Compounds where B and where both A and B are known aryl or heteroaryl fluorescent group were prepared by the addition of a dialkyl or diaryl phosphite to an imine. Standard methodologies are used to prepare imines, particularly the condensation of a primary amine with a substituted aldehyde or ketone. The addition of a dialkyl or diaryl phosphite to an imine can be conducted in a range of solvents well known to those skilled in synthetic chemistry and at temperatures ranging from 20-200° C. It is preferred to conduct the reaction without solvent at temperatures between 60-150° C.

The monoacid esters of Formula 1, where C is a hydroxyl and D is OR$^2$, were prepared from the corresponding di esters by treatment with either mild acid or base. Typically the reactants were dissolved in a solvent and treated with dilute hydrochloric acid or sodium hydroxide at temperatures between 20-100° C. for several hours. The di acids of Formula 1 were prepared via gentle reflux in concentrated hydrochloric acid or via treatment with trimethylsilyl halide in a suitable solvent such as chloroform or dichloromethane. The metal salts of the di acids of Formula 1 were prepared by treatment with base in a suitable solvent followed by a solution of the metal salt. These methodologies are extensively described in the chemical literature. Other derivatives such as amides of Formula 1 were prepared by processes well know to practitioners of synthetic chemistry. For example, the addition of an amine to a phosphoryl chloride derivative of Formula 1 gave the corresponding amide. Metal complex derivatives of Formula 1 can readily be prepared by treatment of a metal salt or complex with the compound of Formula 1 followed by suitable methods of purification.

Metals, metal salts and meal complexes are widely used in a whole host of different manufacturing industries as well as being found throughout nature and the environment. Thus it is important that fluorescent sensors are effective at very low concentrations and in a wide range of solvents, particularly aqueous based, and other media as well as being able to discriminate between various metals and oxidation states. Metals also play an essential role in biology and nutrition and given that minor perturbations of metal ion concentrations can lead to a host of different diseases it is important that fluorescent sensors are effective in aqueous biological fluids. A typical and well-known example of such a fluid is Basal Medium Eagle (BEM), details can be found on www.invitrogen.com. Metal salts of compounds of General Formula 1 can be dissolved in water and in BME in concentration ranges of between 1 pico M to greater than 1 M thus demonstrating the excellent aqueous solubilising effect of the phosphonate group attached to the fluorophores. For example, the di sodium or potassium salt of 8-quinolyloxymethyl phosphonic acid, 4-methylcoumarin-7-oxymethylphosphonic acid, N-carbazolyl methylphosphonic acid and (9-anthracyl)-N-benzylarnine-methylphosphonic acid as well as the octa sodium or potassium salt of 5, 10, 15, 20 tetraphenyl-21H, 24H porphine-p,p',p"p''' tetra oxymethanophosphonic acid are readily soluble in water and various biological media. Compounds of Formula 1 are also very soluble in a wide range of other solvents routinely used in chemical and biological analysis.

Measurements of the fluorescent sensing of compounds of Formula 1 were made by changes to the intensity and/or position of the emission peaks upon addition of a known amount of the metal cation in a range of solvents and biological media. For example the di sodium or potassium salts of 8-quinolyloxy methylphosphonic acid, (9-anthracyl)-N-benzylamine-methylphosphonic acid and N-carbazolyl methylphosphonic acid can sense $Zn^{+2}$ down to concentration between $10^{-8}$-$10^{-12}$M. These sensitivities can be achieved, for compounds of Formula 1, even in the presence of most monovalent metals as well as $Ca^{+2}$ and $Mg^{+2}$.

There are very few examples of fluorescent cupric and vanadyl sensors due to the quenching effects of these paramagnetic metal cations. The diethyl 8-quinolyloxy methylphosphonate can sense both metal cations, cupric and vanadyl down to $10^{-6}$ M concentrations.

To be useful for analysing physiological and biological samples as well as for the identification of biological processes the fluorescent sensors not only have to be soluble in biological media but also have to be able to penetrate cells, membranes and other cytoplasms. Fibrosarcoma cells (cancer cells) were treated with Basal Medium Eagle (BME) containing various examples of phosphonates of Formula 1. The cells were incubated at 37° C. with 5% $CO_2$ for 30 minutes and then the BME solution was removed. The cells were washed with PBS (phosphate buffered saline) and then covered with fresh PBS and then imaged using a Leica DMRD fluorescence microscope. Diethyl 8-quinolyloxy methylphosphonate, diethyl 2-carbazolyloxymethylphosphonate, diethyl N-(tert-butoxycarbonyl)-L-tyrosyl methyl ester methylphosphonate, diethyl 4-(2-benzoxazolyl) phenoxymethylphosphonate, diethyl 5-indolyloxy methylphosphonate, diethyl 4-(1,3diphenyl-5-pyrazolyl) phenoxymethylphosphonate, diethyl N-acridonyloxymethyl phosphonate, diethyl (9-anthracyl)N-benzylamine-methylphosphonate, diethyl (9-anthracyl)N-2,4-dichlorobenzylamine-methylphosphonate and 5, 10, 15, 20-tetrakis (4 diethyl phosphonatomethanoxyphenyl)-21H, 24H porphine as well as the di-sodium salts of 8-quinolyloxy methylphosphonic acid, 4-methylcoumarin 7-oxymethylphosphonic acid, (9-anthracyl)-N-benzylamine-methylphosphonic acid, N-carbazolyl-methylphosphonic acid along with the octa sodium salt of 5, 10, 15, 20-tetraphenyl-21H, 24H porphine-p,p',p",p'''tetra oxymethanophosphonic acid were taken up in the cytoplasm within the fibrosarcoma cells and in some cases into the cell nuclei.

Changes in $Zn^{+2}$ levels have been linked with retarded sexual maturation, Alzheimer's disease, stunted growth and skin damage. Treatment of fibrosarcoma cells with a series of BME solutions containing either diethyl (9-anthracyl)-N-benzylamine-methylphosphonate, or diethyl (9-anthracyl)-N-2,4-dichlorobenzylamine-methylphosphonate with a range of solutions containing increased amounts of $Zn^{+2}$ and then imaged resulted in a progressive increase in fluorescence intensity within the cells.

The brain contains large amounts of chelatable $Zn^{+2}$, present mainly in vesicles within excitatory nerve terminals. $Zn^{+2}$ regulates the function of certain postsynaptic receptors and is a contributing factor in a number of neurological disorders. Slices of rat brain cut into a range of (8, 10, 15, 20, 30 μm) thicknesses were treated with Basal Mediumn Eagle (BME) containing a number of examples of phosphonates of Formula 1. After one hour the slices were washed with PBS (phosphate buffered saline) and then imaged using a Leica DMRD fluorescence microscope. Penetration and selectivity for different parts of the neurological system were observed. For example diethyl 7-oxo-4-methylcoumarin methylphosphonate entered into the endothelial and axon cells but not the neurons cells; the di-sodium salt of N-carbazolylmethylphosphonic acid went into the endothelial and neuronal cells; the di sodium salt of (9-anthracyl)-N-benzylamine-methylphosphonic acid entered the glial and neuronal cells as well as the axon track; diethyl (9-anthracyl)-N-benzylamine-methylphosphonate entered into the caudate putamen and all cells as well as the axon track; and diethyl (9-anthracyl)-N-2,4-dichlorobenzylamine-methylphosphonate went into neurons and glial cells.

Compounds of Formula 1 can also be used to coat a wide range of surfaces including glass, ceramics and apatites. The high affinity of phosphonate for metals results in a strong and stable fluorescent layer on a range of surfaces. This is particularly useful for investigations into the processes involved in the breakdown and wearing of surfaces. These processes can be monitored and measured by assessing the effect of various chemical and biological environments on the appearance, and rate of appearance of the fluorescent phosphonate in the medium including cells, in contact with the surface. Application of N-carbazolylmethylphosphonic acid, (9-anthracyl)-N-benzylamine-methylphosphonic acid or 5, 10, 15, 20-tetraphenyl-21H, 24H porphine-p,p',p",p'''tetra oxyniethanophosphonic acid either as the acid or the corresponding metal salts to hydroxy apatite followed by extensive aqueous washing resulted in a fluorescent layer on the surface.

The invention will now be described in detail with reference to practical examples of the variants according to the invention, taking into account the starting materials that are fimdamentally the most significant.

EXAMPLE 1

To sodium hydride (60%, 0.44 g, 11 mmol, washed with dry hexane) was added dropwise, with stiring under nitrogen, 8-hydroxyquinoline (1.45 g, 10 mmol) in dimethyl sulfoxide (20 ml). After 24 h diethyl 4-chlorophenylsulfonyloxy methylphosphonate (3.6 g, 10.2 mmol) dissolved in dimethyl sulfoxide (14 ml) was added and the solution was stirred for a further 20 h at ambient temperature. The reaction niixture was poured onto water (300 ml) and the mixture was extracted into ethyl acetate (2×200 ml). The combined organic extract was washed with water (2×200 mnl), dried over magnesium sulphate and evaporated to give a viscous oil which was passed down a silica column with first pet.ether—ethyl acetate (2:1) to remove traces of starting materials and then with ethyl acetate to give diethyl 8-quinolyloxy methylphosphonate as a pale yellow oil (2.5 g, 81%), $\delta_H$ (600 MHz, $CD_3OD$) 8.72 (1H, dd, $J_1$ 4.28 Hz, $J_2$ 1.74 Hz), 8.179 (1H, dd, $J_1$ 8.29 Hz, $J_2$ 1.74 Hz), 7.44 (1H, dd, $J_1$ 8.28 Hz, $J_2$ 2.28 Hz), 7.416 (1H, dd, $J_1$ 8.29 Hz, $J_2$ 4.28 Hz), 7.41 (1H, dd, $J_1$ 8.29 Hz, $J_2$ 8.20 Hz), 7.277 (1H, dd, $J_1$ 8.2 Hz, $J_2$ 2.28 Hz), 4.637 (2H, d, J 8.43 Hz), 4.171 (1H, dq, J. 7.2 Hz, $J_2$ 7.1 Hz) and 1.228 (6H, t, J 7.1 Hz), $\delta_P$ (242.94 MHz, $CD_3OD$) 21.46, $\lambda_{ex}$ (ethanol, nm) 344, $\lambda_{em}$ 400, 575.

Metal salts of diethyl 8-quinolyloxy methyl phosphonate were prepared by the following method.

To a solution of diethyl 8-quinolyloxy methyl phosphonate (0.44 g, 1.49 mmols) in ethanol was added a solution of copper nitrate trihydrate (0.36 g, 1.49 mmols) in ethanol to give a dark green solution which afforded a green precipitate which was recrystailised from a mixture of dichloromethane and ethanol to give dark green crystals (0.35 g, 47%), m.p. 125-130° C. Calculated C, 33.57; H, 4.02; N, 8.39; and P, 6.18, found C, 33.20; H, 3.90; N, 8.01 and P, 5.70%, $\lambda_{ex}$ (ethanol, nm) 375, $\lambda_{em}$ 481

To a suspension of copper(II) dichloride (0.23 g, 1.69 mmols) in dry ether (15 ml) was added a solution of diethyl 8-quinolyloxy methylphosphonate (0.50 g, 1.69 mmols) in dry ether (15 ml). The mixture was left to stir under an atmosphere of nitrogen at room temperature for 14 hr. The solvent was removed under vacuum and the precipitate was recrystallised from dichloromethane to give bright green crystals (0.21 g, 27%), m.p. 305-307° C. Calculated C, 37.64; H, 4.50; N, 3.12 and P, 6.92, found C, 37.96; H, 4.01; N, 3.11 and P, 4.75%.

To a suspension of zinc(II) dichlodde (0.24 g, 1.76 mols) in dry ether (20 ml) was added a solution of diethyl 8-quinolyloxy methylphosphonate (0.47 g, 1.59 mmols) in dry ether (10 ml) to form a white precipitate. The mixture was left to stir under an atmosphere of nitrogen at room temperature for 48 hr. The solvent was removed under vacuum and the precipitate was recrystallised from ethanol to give colourless crystals (0.32 g, 44%), m.p. 170-177° C. Calculated C, 38.96; H, 4.20; N, 3.25 and P, 7.18; found C, 38.96; H, 4.12; N, 3.16 and P, 1.87%.

EXAMPLE 2

To a stirred solution of diethyl 8-quinolyloxy methylphosphonate (0.92 g, 3 mmol) dissolved in dry dichloromethane (16 ml) under an atmosphere of nitrogen was added trmethyl silyl iodide (1.8 ml). The red solution was stirred for 2 h then methanol (25 ml) was added. After 2 h the solvent was removed under reduced pressure and then water (20 ml) was added to the residue. The rnixture was concentrated under reduced pressure. Water (20 ml) was added and the mixture was concentrated under reduced pressure. This was repeated four times to afford white needles of 8-quinolyloxy methylphosphonic acid as a half hydrogen iodide salt (0.85 g, 94%), m.p. 285-288° C., $\lambda_{ex}$ (ethanol, nm) 400, $\lambda_{em}$ 418, 493.

EXAMPLE 3

To sodium hydride (60%, 0.85 g, 21 mmol, washed with dry hexane) was added dropwise, with stirig under nitrogen, 7-hydroxy-4-methylcoumarin (3.52 g, 20 mmol) in dimethyl sulfoxide (25 ml). After 24 h diethyl 4-chlorophenylsulfonyloxy methylphospbonate (7.2 g, 20.4 mmol) dissolved in dimethyl sulfoxide (20 ml) was added and the solution was stirred for a further 24 h at ambient temperature. The reaction mixture was poured onto water (300 ml) and then extracted with ethyl acetate (3×100 ml). The combined organic extracts were washed with brine and then dried. Evaporation of the solvent left an oil which on elution from silica with first pet.ether—ethyl acetate (1:1) to remove traces of starting materials and then with ethyl acetate-methanol (95:5) gave diethyl 7-oxomethylphosphonate -4-methylcoumarin (3.6 g, 60%) m.p. 96° C. High Resolution Mass Spec. Found: 327.1004, $C_{15}H_{20}O_6P$ $M^++H$ requires 327.0998. $\delta_P$ (202.46 MHz, $CDCl_3$) 18.99, $\lambda_{ex}$ (DMSO, nm) 349, $\lambda_{em}$ 372; $\lambda_{ex}$ (water, nm) 350, $\lambda_{em}$ 361, 384 and 542.

EXAMPLE 4

Aqueous sodium hydroxide (1M, 15 ml) was added to a solution of diethyl 7-oxymethyl phosphonate-4-methylcoumarin (0.33 g, 1 mmol) dissolved in ethanol (15 ml). The solution was stirred at 50° C. for 5 h and then cooled to room temperature. The solution was acidified with hydrochloric aid (1M) and then stirred for 1 h. The ethanol was removed under reduced pressure and water (50 ml) and ethyl acetate (50 ml) was added to the residue. The organic layer was separated and the aqueous layer was extracted with ethyl acetate (2×50 ml). The combined organic extract was washed with water, dried and concentrated to give ethyl 7-oxymethylphosphonate-4-methylcoumarin as a white solid (0.28 g, 94%), m.p. 177 ° C. ethyl acetate—pet.ether, High Resolution Mass Spec. Found: 299.0676, $C_{13}H_{16}O_6P$ $M^++H$ requires 299.0685, $\delta_H$ (270 MHz, $CDCl_3$) 7.54 (1H, d J 11 Hz, H5)), 6.97 (1H, dd, $J_1$ 11 Hz, $J_2$ 3 Hz, H6), 6.85 (1H, d, J 3 Hz, H8), 6.15 (1H, s, H3), 4.40 (2H, d J 14 Mz, $OCH_2P$), 4.31 (2H, dq, $J_1$ 8 Hz, $J_2$ 8 Hz, $POCH_2$), 2.35 (3H, s, $CCH_3$), 1.41 (3H, t, J 8 Hz, $POCH_2CH_3$), $\delta_P$ (109.3 MHz, $CDCl_3$) 19.76, $\lambda_{ex}$ (water, nm) 357, $\lambda_{em}$ 391, 565.

EXAMPLE 5

To a stired solution of diethyl 7-oxy methylphosphonate-4-methylcoumarin (0.363 g, 1 mmol) dissolved in dry dichloromethane (8 ml) under an atmosphere of nitrogen was added trimethyl silyl iodide (0.85 ml, 5.6 mmols). The red solution was stirred for 2 h then methanol (15 ml) was added. After 2 h the solvent was removed under reduced pressure and then water (20 ml) was added to the residue. The mixture was concentrated under reduced pressure. Water (20 ml) was added and the mixture was concentrated under reduced pressure. This was repeated four times to afford 4-methyl-7-oxymethylphosphonic acid coumarin as a white solid (0.26 g, 95%), m.p. 185-187° C., $\lambda_{ex}$ (water, nm) 355, $\lambda_{em}$ 393, 566.

EXAMPLE 6

To sodium hydride (60%, 0.44 g, 11 mmol, washed with dry hexane) was added dropwise, with stirring under nitrogen, carbazole (1.67 g, 10 mmol) in dimethyl sulfoxide (20 ml). After 1 h diethyl 4-chlorophenylsulfonyloxy methylphosphonate (3.6 g, 10.2 mmol) dissolved in dimethyl sulfoxide (10 ml) was added and the solution was stirred for a further 20 h at ambient temperature. The reaction mixture was poured onto water (200 ml) to give a milky suspension that was acidified with HCl (1M) and then extracted into ethyl acetate (2×200 ml). The combined organic extract was washed with water, dried and then the solvent was evaporated. The residue was passed down a silica column with first pet.ether—ethyl acetate (2:1) to remove traces of starting materials and then with ethyl acetate to give diethyl N-carbazolylmethyl phosphonate as a white solid (2.14 g, 65%), m.p. 75-78° C. High Resolution Mass Spec. Found: 318, 1257, $C_{17}H_{20}NO_3P$ M$^+$+H requires 318.1259. $\delta_P$ (109.3 MHz, CDCl$_3$) 20.6, $\lambda_{ex}$ (water, nm) 338, $\lambda_{em}$ 361, 521 and 540; $\lambda_{ex}$ (DMSO, nm) 349, $\lambda_{em}$ 367, 533 and 547.

EXAMPLE 7

To a stirred solution of diethyl N-carbazolylmethyl phosphonate (0.99 g, 3 mmol) dissolved in dry dichloromethane (10 ml) under an atnosphere of nitrogen was added trimethyl silyl iodide (1.8 ml). The red solution was stirred for 2 h then methanol (15 ml) was added. After 2 h the solvent was removed under reduced pressure and then water (20 ml) was added to the residue. The mixture was concentrated under reduced pressure. Water (20 ml) was added and the mixture was concentrated under reduced pressure. This was repeated four times to afford N-carbazoylymethylphosphonic acid as a white grey solid (0.65 g, 82%), m.p. 245-247° C., High Resolution Mass Spec. Found: 279.0897, $C_{13}H_{12}NO_3P$ M$^+$+NH$_4$ requires 279.0899, $\delta_H$ (270 MHz, DMSO-d$^6$) 8.12 (2H, d, J 7.4 Hz), 7.58 (2H, d, J 8 Hz), 7.42 (2H, dd, $J_1$ 8 Hz, $J_2$ 7.4 Hz), 7.18 (2H, dd, $J_1$ 8 Hz, $J_2$ 7.4 Hz) and 4.59 (2H, d, J 9.4 Hz). $\lambda_{ex}$ (water, nm) 349, $\lambda_{em}$ 370, 537 and 552; $\lambda_{ex}$ (DMSO, nm) 350, $\lambda_{em}$ 371, 555.

EXAMPLE 8

To sodium hydride (60%, 0.44 g, 11 mmol, washed with dry hexane) was added dropwise, with stirring under nitrogen, 2-hydroxycarbazole (1.83 g, 10 mmol) in dimethyl sulfoxide (20 ml). After 24 h diethyl 4-chlorophenylsulfonyloxy methylphosphonate (3.6 g, 10.2 mmol) dissolved in dimethyl sulfoxide (14 ml) was added and the solution was stirred for a further 20 h at ambient temperature. The reaction mixture was poured onto water (300 ml) and a solid (2.95 g) was filtered off. This solid was passed down a silica column with first pet.ether—ethyl acetate (2:1) to remove traces of starting materials and then with ethyl acetate to give diethyl-2-carbazolyloxymethylphosphonate as a pale yellow solid (2.7 g, 81%), m.p. 159° C., High Resolution Mass Spec. Found 333.1122, $C_{17}H_{20}NO_4P$ M$^+$ requires 333.1130, $\delta_P$ (109.3 MHz, DMSO-d$^6$) 20.65, $\lambda_{ex}$ (water, nm) 312, $\lambda_{em}$ 355, 509; $\lambda_{ex}$ (DMSO, nm) 341, $\lambda_{em}$ 358, 537.

EXAMPLE 9

To a stirred solution of diethyl-2-carbazolyloxymethylphosphonate (0.33 g, 1 mmol) dissolved in dry dichloromethane (8 ml) under an atmosphere of nitrogen was added trimethyl silyl iodide (0.6 ml). The red solution was stirred for 2 h then methanol (15 ml) was added. After 2 h the solvent was removed under reduced pressure and then water (20 ml) was added to the residue. The mixture was concentrated under reduced pressure. Water (20 ml) was added and the mixture was concentrated under reduced pressure. This was repeated four times to afford 2-carbazolyloxymethyl phosphonic acid as a yellow green solid (0.26 g, 95%), m.p. 291° C., High Resolution Mass Spec. Pound: 277.0496, $C_{13}H_{12}NO_4P$M$^+$ requires 277.0504. $\delta_H$ (270 MHz, DMSO-d$^6$) 11.13 (1H, s), 7.983 (1H, d, J 5.7 Hz), 7.98 (1H, d, J 5.7 Hz), 7.42 (1H, d, J 8 Hz), 7.28 (1H, dd, $J_1$ 8 Hz, $J_2$ 8 Hz), 7.10 (1H, dd, $J_1$ 8 Hz, $J_2$ 8 Hz), 7.05 (1H, d, J 2 Hz), 6.81 (1H, dd, $J_1$ 8 Hz, $J_2$ 2 Hz), 4.17 (2H, d, J 10.2 Hz), $\lambda_{ex}$ (DMSO, nm) 385, $\lambda_{em}$ 421.

EXAMPLE 10

N-tertbutoxycarbonyl)-L-yrosine methyl ester (2.1 g, 7 mmol) dissolved in dirnethyl sulfoxide (20 ml) was added to sodium hydride (60%, 0.3 g, 7.4 mmol, washed with hexane) and left. to stir for 40 min under nitrogen. Diethyl 4-chlorophenylsulfonyloxy methylphospbonate (2.3 g, 7.2 mmol) dissolved in dimethyl sulfoxide (10 ml) was added and the solution was left to stir for 20 h. The reaction mixture was poured into water (200 ml) and then extracted into ethyl acetate (4×50 ml). The combined organic extract was washed with water dried and concentrated under reduced pressure. The oil was passed down a silica gel column using first pet.ether: ethyl acetate (1:1) to elute traces of starting materials and then with ethyl acetate methanol (95:5) to give diethyl N-(tert-butoxycarbonyl)-L-tyrosyl methyl ester methylphosphonate as an oil (2.95 g, 91%), High Resolution Mass Spec. Found: 446.1953, $C_{20}H_{33}NO_8P$ M$^+$+H requires 446.1944, $\delta_P$ (109.3 MHz, CDCl$_3$) 19.92.

EXAMPLE 11

To sodium hydride (60%, 0.44 g, 11 mmol, washed with dry hexane) was added dropwise, with stirring under nitrogen, 4-acetamidophenol (1.51 g, 10 mmol) in dimethyl sulfoxide (15 ml). After 24 h diethyl 4-chlorophenylsulfonyloxy methylphosphonate (3.5 g, 10.2 mmol) dissolved in dimethyl sulfoxide (10 ml) was added and the solution was stirred for a further 20 h at ambient temperature. The reaction mixture was poured onto water (300 ml) and then extracted with ethyl acetate (3×100 ml). The combined organic extracts were washed with brine and then dried. Evaporation of the solvent left an oil which on elution from silica with first pet.ether—ethyl acetate (1:4) to remove traces of starting materials and then with ethyl acetate gave diethyl 4-acetamidophenoxy methylphosphonate (2.4 g, 80%) as white needles rnp. 95° C., High Resolution Mass Spec. Found: 302.1145, $C_{13}H_{21}NPO_5P$ M$^+$+H requires 302.1157, $\delta_P$ (CDCl$_3$) 19.92, $\lambda_{ex}$ (water, nm) 355, $\lambda_{em}$ 364, 521.

EXAMPLE 12

To sodium hydride (60%, 0.44 g, 11 mmol, washed with dry hexane) was added dropwise, with stirring under nitrogen, 1-(3-hydroxyphenyl) urea (1.52 g, 10 mmol) in dimethyl sulfoxide (15 ml). After 24 h diethyl 4-chlorophenylsulfonyloxy methylphosphonate (3.5 g, 10.2 mmol) dissolved in dimethyl sulfoxide (10 ml) was added and the solution was stirred for a further 10 h at ambient temperature. The reaction mixture was poured onto water (300 ml) and then extracted with ethyl acetate (3×100 ml). The combined organic extracts were washed with brine and then dried. Evaporation of the solvent left an oily solid which on crystallization from pet.ether—ethyl acetate gave diethyl 3-urea-1-phenoxy methylphosphonate as white needles (2.5 g, 83%) m.p. 135° C., High Resolution Mass Spec. Found: 303.1102, $C_{12}H_{20}N_2O_5P$M$^+$+H requires 303.1110, $\lambda_{ex}$ (DMSO, nm) 332, $\lambda_{em}$ 394, 403, 414.

EXAMPLE 13

To sodium hydride (60%, 0.25 g, 5.5 mmol, washed with dry hexane) was added dropwise, with stirring under nitrogen, 2-benzothiazoletbiol (0.93 g, 5.5 mmol) in dimethyl suffoxide (10 ml). After 1 h diethyl 4-chlorophenylsulfonyloxy methylphosphonate (1.77 g, 5.5 mmol) dissolved in dimethyl sulfoxide (20 ml) was added and the solution was stirred for a further 48 h at ambient temperature. The reaction mixture was poured onto water (100 ml) and then extracted with ethyl acetate (3×100 ml). The combined organic extracts were washed with brine and then dried. Evaporation of the solvent left an oily solid, which on elution from silica, first with pet.ether—ethyl acetate (1:1) to remove traces of starting materials and then with ethyl acetate gave diethyl 2-benzothiazolesulfinyl methylphosphonate as a viscous oil (1.2 g, 63%), High Resolution Mass Spec. Found: 318.0401, $C_{12}H_{17}NO_3PS_2M^++H$ requires 318.0388, $\delta_H$ 7.85 (1H, d, J 8 Hz), 7.73 (1H, d, J 8 Hz), 7.4 (1H, m), 7.29 (1H, m), 4.13 (4H, dq, $J_1$ 7 Hz, $J_2$ 7 Hz), 3.79 (2H, d, J 15 Hz), 1.27 (6H, t, J7 Hz), $\delta_P$ 22.02.

EXAMPLE 14

To sodium hydride (60%, 0.44 g, 11 mmol, washed with dry hexane) was added dropwise, with stirring under nitrogen, 4-(2-benzoxazolyl) phenol (2.11 g, 10 mmol) in dimethyl sulfoxide (15 ml). After 24 h diethyl 4-chloropbenylsulfonyloxy methylphosphonate (3.5 g, 10.2 mmol) dissolved in dinrethyl sulfoxide (10 ml) was added and the solution was stirred for a further 24 h at ambient temperature. The reaction mixture was poured onto water (300 ml) and then extracted with ethyl acetate (3×100 ml). The combined organic extracts were washed with brine and then dried. Evaporation of the solvent left an oily solid that on elution from silica, first with pet.ether—ethyl acetate (1:1) to remove traces of starting materials and then with ethyl acetate gave diethyl 4-(2-benzoxazolyl) phenoxymethylphosphonate as an oil (1.85 g, 51%), $\delta_H$ (270 MHz, CDCl$_3$) 8.20 (2H, d, J 9 Hz), 7.74 (1H, m), 7.56 (1H, m), 7.33 (2H, m), 7.09 (2H, d, J 9 Hz), 4.31 (2H, d, J 13 Hz), 4.26 (4H, dq, $J_1$ 7Hz, $J_2$ 7 Hz) and 1.36 (6H, t, J 7 Hz), $\delta_P$ (109.7 MHz, CDCl$_3$) 19.23, $\lambda_{ex}$ (EtOH, nm) 368, $\lambda_{em}$ 399, 568 and 602.

EXAMPLE 15

A solution of 5-hydroxyindole (1.0 g, 7.5 mmol) in dimethyl sulfoxide (15 ml) was added to sodium hydride (60%, 0.3 g, 7.5 mmol, washed with hexane) and left to stir for 2 h under nitrogen. Diethyl 4-chlorophenylsulfonyloxy methylphosphonate (2.65 g, 7.5 mmol) dissolved in dimethyl sulfoxide (20 ml) was added and the solution was left to stir for 48 h. The reaction mixture was poured into water (200 ml), acidified and then extracted into ethyl acetate (2×100 ml). The combined organic extract was washed with water dried and concentrated under reduced pressure. The oil was passed down a silica gel column using first pet.ether:ethyl acetate (1:1) to elute traces of staring materials and then with ethyl acetate:pet ether (5:1) to elute diethyl 5-indolyloxy methylphosphonate (1.80 g, 85%) as an off white solid, m.p 70° C. $\delta_H$(270 MHz, CDCl$_3$) 9.44 (1H, bs), 7.28 (1H, d, J 9 Hz), 7.16 (2H, bs), 6.85 (1H, dd, $J_1$ 9 Hz, $J_2$ 2 Hz), 6.42 (1H, bs), 4.35 (2H, d, J 9.5 Hz), 4.24 (4H, dq, $J_1$7.5 Hz, Jz 7.5 Hz), 1.34 (6H, t, J 7.5 Hz), $\delta_P$ (109.3 MHz, CDCl$_3$) 21.12, $\lambda_{ex}$ (DMSO, nm) 313, $\lambda_{em}$ 337, 495, $\lambda_{ex}$ (water, nm) 312, $\lambda_{em}$ 343, 385.

EXAMPLE 16

A solution of 4-(1,3-diphenyl-5-pyrazolyl) phenol (2.34 g, 7.5 mmol) in dimethyl sulfoxide (15 ml) was added to sodium hydride (60%, 0.3 g, 7.5 mmol, washed with hexane) and left to stir for 2 h under nitrogen. Diethyl-chlorophenylsulfonyloxy methylphosphonate (2.65 g, 7.5 mmol) dissolved in dimethyl sulfoxide (20 ml) was added and the solution was left to stir for 10 h. The reaction mixture was poured into water (200 ml), acidified and then extracted into ethyl acetate (2×100 ml). The combined organic extract was washed with water dried and concentrated under reduced pressure. The oil was passed down a silica gel column using fsrst pet.ether: ethyl acetate (1:1) to elute traces of starting materials and then with ethyl acetate to elute diethyl 4-(1,3-diphenyl-5-pyrazolyl) phenoxy methylphosphonate (1.80 g, 51%), $\lambda_{ex}$ (Toluene, nm) 322, $\lambda_{em}$ 375, 516, $\lambda_{ex}$ (ethanol, nm) 315, $\lambda_{em}$ 378

EXAMPLE 17

A solution of 9-(10H) acridone (0.97 g, 5 mmol) in dirnethyl sulfoxide (10 ml) was added to sodium hydride (60%, 5 mmol, washed with hexane) and left to stir for 1 h under nitrogen. Diethyl 4-chlorophenylsulfonyloxy methylphosphonate (1.8 g, 5 mmol) dissolved in dimnethyl sulfoxide (10 ml) was added and the solution was left to stir for 10 h. The reaction mixture was poured into water (200 ml), acidified and then extracted into ethyl acetate (2×100 ml). The combined organic extract was washed with water dried and concentrated under reduced pressure. The oil was passed down a silica gel column using first petether: ethyl acetate (1:1) to remove traces of starting materials and then with ethyl acetate:methanol (1:3) to elute diethyl N-acridonyloxymethyl phosphonate (1.0 g, 56%), $\delta_P$ (109.3 MHz, CDCl$_3$) 19.61, $\lambda_{ex}$ (ethanol, nm) 352, $\lambda_{em}$ 435.

EXAMPLE 18

A solution of 1,1'-bi-2-naphthol (2.66 g, 10 mmol) in dimethyl suloxide (40 ml) was added to sodium hydride (60%, 0.88 g, 22 mmol, washed with hexane) and left to stir for 24 h under nitrogen. Ac white solid precipitated from the reaction mixture. Diethyl 4-chlorophenyl sulfonyloxy methylphosphonate (7.0 g, 20 mmol) dissolved in dimethyl sulfoxide (25 ml) was added and the solution was left to stir for 14 h. The solid dissolved after 2 h. The reaction mixture was poured into water (200 ml) and then extracted into ethyl acetate (4×70 ml). The combined organic extract was washed with water dried and concentrated under reduced pressure. The oil was passed down a silica gel column using first pet-ether: ethyl acetate (1:1) to elute traces of the starting materials and then with ethyl acetate: pet ether (5:1) to elute 2-(diethyl phosphonatomethanoxy)-1-(naphthyl-2-ol) naphthalene (1.5 g), m.p. 194° C., High Resolution Mass Spec. Found: 437.1526, $C_{25}H_{26}O_5P$ M$^+$+H requires 437.1518, and then with ethyl acetate : methanol (95:5) to elute 1,1'- bi -2-diethyl phosphonatomethanoxy naphthalene (1.1 g) m.p. 74° C., $\delta_P$ 19.27 broad, optical isomer $\delta_P$ 18.93 sharp, High Resolution Mass Spec. Found: 587.1952, $C_{30}H_{37}O_8P_2M^++H$ requires 587.1964.

EXAMPLE 19

Sodium hydroxide (1M, 18 ml) was added to a solution of 2-(diethyl phosphonatomethanoxy)-1-(naphthyl-2-ol) naphthalene (0.33 g, 0.75 mmol) in ethanol (18 ml). The solution was stirred at 50° C. for 5 h under an atmosphere of nitrogen and then concentrated under reduced pressure. Water (30 ml) was added to the residue and the mixture was acidified with hydrochloric acid (1 M) and then extracted with ethyl acetate (2×50 ml). The combined organic extract was washed with water, dried and concentrated to give a pale white solid 2-ethyl phosphonato methanoxy)-1-naphthyl-2-ol) naphthalene (0.29 g, 94%), m.p. 72° C., High Resolution Mass Spec. Found: 409.1214, $C_{23}H_{22}O_5P$ M$^+$+H requires 409.1205. $\delta_P$ (109.3 MHz, CDCl$_3$) 18.93.

EXAMPLE 20

In a one-necked 100 ml flask a mixture containing 9-anthraldehyde (4.12 g, 20 mmol), benzyl amine (20 mmol) and ethanol (20 ml) was gently refluxed with stiring for 4 h. After cooling to room temperature the ethanol was removed under reduced pressure. Diethyl phosphite (2.9 ml, 22 mmol) was added and the mixture was heated at a bath temperature of 120° C. for 12 h. After cooling to room temperature the residue was dissolved in ethyl acetate (200 ml) and washed with 5% sodium carbonate solution (2×25 ml) and then with water (50 ml). The organic layer was dried over magnesium sulphate, filtered and then the solvent was evaporated under reduced pressure. The material was passed down a short flash silica gel column with pet.ether—ethyl acetate mixtures—starting with 9:1 ratio to elute traces of the starting materials and then with ethyl acetate to elute diethyl (9-anthracyl)-N-benzylamine-methylphosphonate (7.8 g, 90%), High Resolution Mass Spec. Found: 434.1884 $C_{23}H_{22}O_5P$ M$^+$+H requires 434.1885, $\delta_P$ (109.3 MHz, CDCl$_3$) 2533, $\lambda_{ex}$ (EtOH, nm) 390, $\lambda_{em}$ 420.

EXAMPLE 21

A mixture of diethyl (9-anthracyl)-N-benzylamine-methylphosphonate (0.44 g) and Analar concentrated hydrochloric acid (10 ml) was stirred at gentle reflux for 5 h. Cooled, the solvent was then removed under reduced pressure. Water (10 ml) was added and the solvent was removed under reduced pressure. This was repeated a further four times to give (9-anthracyl)-N-benzylamine-methylphosphonic acid as a white solid (0.4 g), m.p. 168-170° C., $\lambda_{ex}$ (EtOH, nm) 332, $\lambda_{em}$ 425.

EXAMPLE 22

In a one-necked 100 ml flask a mixture containing 9-anthraldehyde (4.12 g, 20 mmol), 2,4-dichlorobenzyl amine (20 mmol) and ethanol (20 ml) was gently refluxed with stirring for 4 h. After cooling to room temperature the ethanol was removed under reduced pressure. Diethyl phosphite (2.9 ml, 22 mmol) was added and the mixture was heated at a bath temperature of 120° C. for 12 h. After cooling to room temperature the residue was dissolved in ethyl acetate (200 ml) and washed with 5% sodium carbonate solution (2×25 ml) and then with water (50 ml). The organic layer was dried over magnesium sulphate, filtered and then the solvent was evaporated under reduced pressure. The material was passed down a short flash silica gel column with pet.etber—ethyl acetate mixtures—starting with 9:1 ratio to elute traces of the starting materials and then with ethyl acetate to elute diethyl (9-anthracyl)-N-2,4-dichlorobenzylamine-methylphosphonate (8.05 g, 80%), m.p. 85-87° C., $\delta_P$ (109.3 MHz, CDCl$_3$) 24.81, $\lambda_{ex}$ (EtOH, nm) 336, $\lambda_{em}$ 421, 625.

EXAMPLE 23

In a one-necked 100 ml flask a mixture containing 9-anthraldehyde (4.12 g, 20 mmol), 3-methoxypropyl amine (20 mmol) and ethanol (20 ml) was gently refluxed with stirring for 4 h. After cooling to room temperature the ethanol was removed under reduced pressure. Diethyl phosphite (2.9 ml, 22 mmol) was added and the mixture was heated at a bath temperature of 120° C. for 12 h. After cooling to room temperature the residue was dissolved in ethyl acetate (200 ml) and washed with 5% sodium carbonate solution (2×25 ml) and then with water (50 ml). The organic layer was dried over magnesium sulphate, filtered and then the solvent was evaporated under reduced pressure. The material was passed down a short flash silica gel column with pet.ether—ethyl acetate mixteres—starting with 9:1 ratio to elute traces of the starting materials and then with ethyl acetate-methanol (1:1) to elute diethyl (9-anthracyl) N-(3-methoxy)propylamine-methylphosphonate (6.5 g, 78%), $\lambda_{ex}$ (EtOH, um) 330, $\lambda_{em}$ 418.

EXAMPLE 24

In a one-necked 100 ml flask a mixture containing 9-anthraldehyde (4.12 g, 20 mmol), N,N diethylamine ethylamine (20 mmol) and ethanol (20 ml) was gently refluxed with stirng for 4 h. After cooling to room temperature the ethanol was removed under reduced pressure. Diethyl phosphite (2.9 ml, 22 mmol) was added and the mixture was heated at a bath temperature of 120° C. for 12 h. After cooling to room temperature the residue was dissolved in ethyl acetate (200 ml) and washed with 5% sodium carbonate solution (2×25 ml) and then with water (50 ml). The organic layer was dried over magnesium sulphate, filtered and then the solvent was evaporated under reduced pressure. The material was passed down a short flash silica gel column with pet.ether—ethyl acetate mixtures—starting with 1:1 ratio to elute traces of the starting materials and then with ethyl acetate-methanol (1:2) to elute diethyl (9-anthracyl)-N-(2-N,N diethylamine ethylamine)-methylphosphonate (6.0 g, 90%), $\lambda_{ex}$ (EtOH, nm) 326, $\lambda_{em}$ 420.

EXAMPLE 25

In a one-necked 100 ml flask a mixture containing 9-anthraldehyde (4.12 g, 20 mmol), n-butylamine (20 mmol) and ethanol (20 ml) was gently refluxed with stirring for 3 h. After cooling to room temperature the ethanol was removed under reduced pressure. Diethyl phosphite (2.9 ml, 22 mmol) was added and the mixture was heated at a bath temperature of 110° C. overnight. After cooling to room temperature the residue was dissolved in ethyl acetate (100 ml) and washed with 5% sodium carbonate solution (3×50 ml) and then with water (150 ml). The organic layer was dried over magnesium sulphate, filtered and then the solvent was evaporated under reduced pressure. The material was passed down a flash silica gel column with pet.ether—ethyl acetate mixtures—starting with 9.5:0.5 to elute traces of the starting materials and then with pet.ether—ethyl acetate (7:3) to elute diethyl (9-anthracyl)-N-butylamine methylphosphonate as an oil (4.83 g, 60%), $\delta_P$ (109.3 MHz, CDCl$_3$) 25.5, $\lambda_{ex}$ (EtOH, nm) 331, $\lambda_{em}$ 418.

EXAMPLE 26

To sodium hydride (60%, 0.44 g, 11 mmol, washed with dry hexane) was added dropwise, with stinrng under nitrogen, 4-hydroxybenzaidehyde (1.22 g, 10 mmol) in dimethyl sulfoxide (15 ml). After 2 h diethyl 4-chlorophenylsulfonyloxy methyl-phosphonate (3.5 g, 10.2 mmol) dissolved in dimethyl sulfoxide (10 ml) was added and the solution was stirred for a further 12 h at room temperature. The reaction mixture was poured onto water (300 ml) and then extracted with ethyl acetate (3×50 ml). The combined organic extracts were washed with brine and then dried. The solvent was removed under reduced pressure and the residue was passed down a flash silica gel column with first pet.ether—ethyl acetate (1:4)

to remove traces of starting materials and then with ethyl acetate to give diethyl 4-carbonylphenoxy methylphosphonate as an oil (2.4 g, 88%). High Resolution Mass Spec. Found: 273.0900, $C_{12}H_{18}O_5P$ $M^++H$ requires 273.0892. $\delta_H$ (270 MHz, $CDCl_3$) 9.88 (1H, s), 7.83 (2H, d, J 8.9 Hz), 7.06 (2H, d, J 8.9 Hz), 4.32 (2H, d, J 10.1 Hz), 4.22 (4H, dq, $J_1$ 7.2 Hz, $J_2$ 7.2 Hz), 1.34 (6H, t, J 7.2 Hz).

On standing in air diethyl 4-carbonylphenoxy methylphosphonate deposited 4-diethyl phosphonato methanoxy benzoic acid as a white solid, m.p. 110° C., decarboxylates >200° C., High Resolution Mass Spec. Found: 289.0853, $C_{12}H_{18}O_6P M^++H$ requires 289.0841, $\delta_P$ ($CDCl_3$) 19.23.

EXAMPLE 27

A mixture containing freshly fused potassium carbonate (0.8 g, 5.8 mmol), 5, 10, 15, 20-tetrakis (4- hydroxyphenyl)-21H, 24H porphine (0.25 g, 0.37 mmol) and diethyl 4-chlorophenylsulfonyloxy methyl phosphonate (2.06 g, 5.9 mmol) in DMSO (20 ml) was stirred at 50° C. under an atmosphere of nitrogen for 12 h. After cooling the reaction mixture was poured onto water (100 ml) and then extracted into chloroform (2×150 ml). The combined organic layers were washed with water, dried and the solvent was removed under reduced pressure. The residue was passed down a flash silica gel column first with ethyl acetate to remove the excess diethyl 4-chlorophenyl sulfonyloxy methyl phosphonate and then with ethyl acetate-methanol (4:1) to give 5, 10, 15, 20-tetrakis (4 diethyl phosphonatomethanoxyphenyl)-21H, 24H porphine as a deep purple solid (0.43 g, 91%), High Resolution Mass Spec.: Found: 1279.4170, $C_{64}H_{75}N_4O_{16}P_4 M^++H$ requires 1279.4129, $\delta_P$ 20.0, $\lambda_{max}$ (tetrahydrofuran, nm) ($\epsilon$, $dm^3$ $mol^{-1}$ $cm^{-1}$) 420 (603,017), 516 (19,197), 552 (12,748), 594 (5,999), 651 (6,699).

EXAMPLE 28

A mixture containing 5, 10, 15, 20-tetrakis (4 diethyl phosphonatomethanoxyphenyl)-21H, 24H porphine (0.065 g, 0.05 mmol) and zinc acetate (0.13 g) in chloroform (10 ml) was refluxed under an atmosphere of nitrogen for 24 h. On cooling chloroform (50 ml) and water (50 ml) was added and the separated organic layer was washed with water (3×50 ml), dried and concentrated under reduced pressure. The residue was passed down a short flash silica gel column with ethyl acetate-methanol (10:1) to give 5, 10, 15, 20-tetrakis (4 diethyl phosphonatomethanoxyphenyl)-21H, 24H porphine zinc(II) as a purple powder (0.062 g, 91%), $\delta_H$ (600 MHz) 8.89 (8H, s), 8.09 (8H, d, J 8.7 Hz), 7.21 (8H, d, J 8.7 Hz), 3.82 (24H, bm) and 1.21 (24H, t, J 7.2 Hz), $\delta_P$ 19.36, $\lambda_{max}$ (tetrahydrofuran, nm) ($\epsilon$, $dm^3$ $mol^{-1}$ $cm^{-1}$) 426 (475,588), 558 (14,145), 598 (7,358).

EXAMPLE 29

Trimethyl silyl iodide (0.36 ml, 2.5 mmol) was added to 5, 10, 15, 20-tetrakis (4 diethyl phosphonatomethanoxyphenyl)-21H, 24H porphine (0.1 g, 0.078 mmol) dissolved in dichloromethane (12 ml) and the solution was stirred for 2 h under an atmosphere of nitrogen. Methanol (2 ml) was added and the solution was stirred for a further 2 h. The solvents were removed under reduced pressure. Water (20 ml) was added and then removed under reduced pressure. This was repeated a further four times to afford 5, 10, 15, 20-tetraphenyl-21H, 24H porphine-p,p',p'',p'''tetra oxymethanophosphonic acid as a green powder (0.074 g, 90%), $\delta_H$ (DMSO-$d_6$) 8.86 (8H, s), 8.14 (8H, d, J 8.6 Hz), 7.46 (8H, d, J 8.6 Hz), 4.42 (8H, d, J 10.6 Hz), $\delta_P$ (DMSO-$d_6$) 15.37. As octa sodium salt prepared using NaOD $\delta_P$ ($D_2O$) 13.26, $\lambda_{max}$ (water, nm) ($\epsilon$, $dmd^3$ $mol^{-1}$ $cm^{-1}$) 421 (219,019), 522 (6,858), 563 (6,312), 585 (3,956), 642 (3,662).

EXAMPLE 30

Diethyl 4-chlorophenylsulfonyloxy methyl-phosphonate (3.5 g, 10.2 mmol) dissolved in dimethyl sulfoxide (10 ml) was added to a solution of sodium 7-hydroxy-3-H-phenoxazin-3-one (2.35 g, 10 mmol) in DMSO (15 ml) and the resultant solution was stirred for a further 12 h at room temperature. The reaction mixture was poured onto water (300 ml) and then extracted with ethyl acetate (3×50 ml). The combined organic extracts were washed with brine and then dried. The solvent was removed under reduced pressure and the residue was passed down a flash silica gel column with ethyl acetate to afford 4-diethyl phosphonatomethanoxy 3-H-phenoxazin-3-one as an oil (2.54 g, 70%), $\delta_P$ (109.3 MHz, $CDCl_3$) 19.1.

EXAMPLE 31

An ethanolic solution (1 mM) of the product from Example 1 was prepared and a fluorescence spectrum run; excitation $\lambda_{ex}$ 342 nm and gave emission peaks ($\lambda_{em}$) at 400 and 575 nm. Titration experiments were conducted by adding known quantities of metal salts and the emission spectrum were recorded after each addition.

$Mg^{+2}$ and $Ca^{+2}$ had no significant effect on the fluorescent intensity. There was a large decrease in emission intensity on the first addition of $Ni^{+2}$, $Co^{+2}$ and $Mn^{+2}$ with subsequent decrease on following additions. $SrCl_2$ caused a 50% increase in fluorescence intensity after addition of 1 equivalent. $Zn^{+2}$ demonstrated a four-fold increase in fluorescence intensity after addition of one equivalent along with shifts to lower energy. The diethyl 8-quinolyloxy methyl phosphonate can sense $Zn^{+2}$ down to 60 ηM On the addition of $VO^{+2}$, a drcrease in the emission intensity was observed at the 400 nm peak, on the additon of 0.1 eq of $VO^{+2}$, there was the appearance of a new peak at 500 nm that increases in intensity with subsequent additions of $VO^{+2}$ until 0.5 eq after which it plateaus off. On the addition of $Cu^{+2}$, a decrease in intensity is again observed for the two peaks at 400 and 575 nm, with the appearance of a new peak at 500 nm, and this reaches a plateau after the addition of 0.4 eq.

EXAMPLE 32

An aqueous solution (1 mM) of the di-sodium salt of the product from Example 2 was prepared by the addition of 3 equivalents of 1 M NaOH in water. A fluorescence spectrum was run on the resultant solution; excitation $\lambda_{ex}$ 400 nm and gave emission peaks ($\lambda_{em}$) at 418 and 493 nm. Titration experiments were conducted by adding known quantities of metal salts and the emission spectrum were recorded after each addition.

Calcium—$Ca^{+2}$:

Micro litre aliquots of an aqueous calcium nitrate (1 mM) were added to the above solution. A twenty six-fold increase in fluorescent intensity of the solution was observed on addition of 0.015 equivalents of calcium nitrate. This di sodium 8-quinolyloxy methyl phosphonate solution can sense, significant and reproducible increase in fluorescent intensity, $Ca^{+2}$ concentrations down to $10^{-10}$M.

Vanadyl—$VO^{+2}$

Micro litre aliquots of an aqueous vanadyl sulfate (1 mM) were added to the above solution. A 30% increase in fluorescent intensity of the solution was observed on addition of 2 μl of vanadyl sulfate (1 mM). This di sodium 8-quinolyloxy methyl phosphonate solution can sense, significant and reproducible increase in fluorescent intensity, $VO^{+2}$ concentrations down to $10^{-9}$M.

Zinc—$Zn^{+2}$

Micro litre aliquots of an aqueous zinc nitrate (1 mM) were added to the above solution. A 30% increase in fluorescent intensity of the solution was observed on addition of 2 μl of zinc nitrate (1 mM). This di sodium 8-quinolyloxy methyl phosphonate solution can sense, significant and reproducible increase in fluorescent intensity, $Zn^{+2}$ concentrations down to $10^{-12}$ M.

EXAMPLE 33

A fluorescence spectrum was run on an ethanolic solution (1 mM) of the product from Example 20; sample size 3.5 ml, with excitation wavelength $\lambda_{ex}$ 339 nm to give emission peaks $\lambda_{em}$ at 411 nm. Titration experiments were conducted by adding known quantities (μl of a 0.1 M $ZnCl_2$ solution) of metal salts and the emission spectrum were recorded after each addition. A 30% increase in fluorescent intensity of the solution was observed on addition of one equivalent of zinc nitrate. This diethyl (9-anthracyl)-N-benzylamine-methylphosphonate solution could sense, significant and reproducible increase in fluorescent intensity, $Zn^{+2}$ concentrations down to $10^{-7}$M.

EXAMPLE 34

An ethanolic solution (1 mM) of the di-sodium salt of the product from Example 21 was prepared by the addition of 2 equivalents of 1 M NaOH in water. A fluorescence spectrum was run on the resultant solution; excitation $\lambda_{ex}$ 328 nm and gave emission peaks ($\lambda_{em}$) at 422 nm. Titration experiments were conducted by adding known quantities (μl of a 0.1 M $ZnCl_2$ solution) of metal salts and the emission spectrum were recorded after each addition. A two and a half fold increase in fluorescent intensity of the solution was observed on addition of one equivalent of zinc nitrate. This di sodium (9-anthracyl)-N-benzylamine-methylphosphonate solution could sense, significant and reproducible increase in fluorescent intensity, $Zn^{+2}$ concentrations down to $10^{-8}$M.

EXAMPLE 35

A solution (1 mM) of the di-sodium salt of the product from Example 7 was prepared by the addition of 2 equivalents of 1 M NaOH in water. A fluorescence spectrum was ran on the resultant solution; excitation $\lambda_{ex}$ 350 nm and gave emission ($\lambda_{em}$) at 370 nm. Titration experiments were conducted by adding known quantities of metal salt solutions and the emission spectrum were recorded after each addition. An eight-fold increase in fluorescent intensity of the solution was observed on addition of one equivalent of zinc nitrate. This di sodium N-carbazolylmethylphosphonate solution could sense, significant and reproducible increase in fluorescent intensity, $Zn^{+2}$ concentrations down to $10^{-12}$ M. Using the same methodology for $Ca^{+2}$ and $Mg^{+2}$ only increases of 5 and 8% respectively of fluorescent intensity was observed on addition of one equivalent of metal cation.

EXAMPLE 36

The di-sodium salt of the product from Example 7 was prepared by the addition of 2 equivalents of 1 M NaOH in water. This was then used to prepare a di sodium N-carbazolylmethylphosphonate (50 μM/L) solution in Basal Medium Eagle. A fluorescence spectrum was run on the resultant solution; $\lambda_{ex}$ 350 nm and gave emission ($\lambda_{em}$) at 370 nm. Known quantities of a zinc chloride solution were then added and the emission spectrum was recorded after each aliquot. Addition of 2ηM $Zn^{+2}$ resulted in a reproducible increase in fluorescent intensity of 30% in the peak at 370 nm and addition of 2 μM of $Zn^{+2}$ gave a 2-fold increase in intensity.

EXAMPLE 37

Fibrosarcoma cells were placed in a two series of wells and a diethyl (9-anthracyl)-N-benzylamine-methylphosphonate solution in BME (100 μl, 50 μM) was added to the first and a diethyl (9-anthracyl)-N-2,4-dichlorobenzylamine-methylphosphonate solution in BME (100 μl, 50 μM) to the second and left for 30 min. To each series was added portions (0.5, 1, 2, 5, 20 μl) of a zinc chloride solution and the cells were incubated at 37° C. in an environment containing carbon dioxide (5%). The phosphonate-Zn solution was removed and the wells washed with PBSphosphate-buffered saline- to remove the last traces of phosphonate then imaged. Fluorescence images, using a Leica DMRD fluorescence microscope, were then run on each of the samples in the wells. For both phosphonates progressive, significant and reproducible increases in fluorescence intensity were observed going from 0.5 up to 5 μl of added zinc solution. Addition of excess TPEN, N,N,N',N'-tetrakis(2-pyridylmethyl)ethylenediamine, to any of the wells resulted in a very significant quenching of the fluorescence. TPEN is a very strong chelator of $Zn^{2+}$ cations, thus removing all free zinc.

EXAMPLE 38

Solutions (5 ml, 1 mM) of the di-sodium salt of the products of Example 7 and 21 as well as the octa-sodium salt of Example 29 were each treated with hydroxyapatite (100 mg) and the resultant mixtures were stirred at room temperature for 10 h. The hydroxyapatite was then filtered and washed well with water till the washings were no longer fluorescent Analysis of these hydroxyapatite samples showed that a fluorescent coating had been applied in each case.

EXAMPLE 39

An aqueous solution (100 μM) of the N-carbazolylmethylphosphonic acid—Example 7—was applied with warm air drying to a samples of powder or annealed hydroxyapatite. The hydroxyapatite was then washed well with water and analysed. A fluorescent layer had been deposited on the surface of the hydroxyapatite.

EXAMPLE 40

Dicyclohexyl carbodiimide (40 mg) dissolved in DMF (0.5 ml) was added to a solution of adenosine 2, 3 isopropylidene (32 mg) and 4-methyl-7-oxymethylphosphonic acid coumarin (27 mg) in DMF (1 ml). The solution was stirred at room temperature for 4 h and during this time a white solid precipitated from the solution. The mixture was filtered and the solid was washed with a little DMA. The solvent was evaporated and the residue was washed with ether to remove unreacted dicyclohexyl carbodiimide. The residue was then dried to give 4-methyl-7-oxymethylpbosphonic acid coumarin substituted adenosine.

The invention claimed is:

1. A compound of General Formula 1:

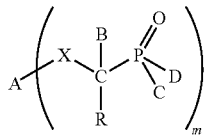

Formula 1 wherein:
R is hydrogen or a linear or branched $C_{1-40}$ alkyl;
X is O, S, or $NR^1$ where $R^1$ is a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group;
one or both of C and D is $OR^2$, $SR^2$, $NR^3R^4$ where $R^2$, $R^3$, and $R^4$ are each independently hydrogen, a linear or branched $C_{1-40}$ alkyl, $C_{2-40}$ alkenyl or $C_{2-40}$ alkynyl group, an aryl or $C_{1-40}$ alkylaryl group or a linear or branched $C_{1-40}$ alkyl $NR^5R^6$ chain where $R^5$ and $R^6$ are each independently hydrogen, a linear or branched $C_{1-40}$ alkyl or an optionally complex metal ion $M^{n+}/n$ wherein n is an integer from 1 to 8;
m is 1;
A is chosen from acridine, coumarin, carbazole, quinolone, indolyl, bipyridyl, thiazole, and benz-2-oxa-1,3-diazole, wherein A may be substituted with one or more substituents chosen from nitro, chloro, fluoro, bromo, nitrile, sulfonic acid or salt of sulfonic acid, carboxy, carboxyalkyl, carboxyalkoxy, carboxylalkylamino, carboxyalkylthio, $C_{1-6}$-alkoxy, di $C_{1-40}$ alkyl phosphonate, $C_{1-40}$ alkyl phosphonate, phosphonic acid, amino, amino $C_{1-40}$ alkyl, and amino di ($C_{1-40}$-alkyl); and
B is hydrogen, a linear or branched $C_{1-40}$ alkyl, $C_{2-40}$ alkenyl or $C_{2-40}$ alkynyl group, an aryl, a heteroaryl or $C_{1-40}$ alkylaryl or alkylheteroaryl group.

2. A compound as claimed in claim 1 where R is hydrogen or a linear or branched $C_{1-10}$ alkyl.

3. A compound as claimed in claim 1 wherein:
X is O, S, or $NR^1$ where $R^1$ is a linear or branched $C_{1-10}$ alkyl;
R is hydrogen or a linear or branched $C_{1-10}$ alkyl;
B is a hydrogen or a linear or branched $C_{1-10}$ alkyl; and
one or both of C and D is $OR^2$, $NR^3R^4$ where $R^2$, $R^3$, and $^4$ are each independently hydrogen, a linear or branched $C_{1-10}$ alkyl, or an optionally complex metal ion $M^{n+}/n$ wherein n is an integer from 1 to 8, or a linear or branched $C_{1-10}$ alkyl $NR^5R^6$ chain where $R^5$ and $R^6$ are each independently hydrogen, a linear or branched $C_{1-10}$ alkyl.

4. A compound as claimed in claim 1, wherein $M^{n+}$ is derived from a lanthanide, actinide, main group or transition metal.

5. A method of detecting, discriminating, or quantifying metal cations in a wide range of solvents, chemical and waste streams, physiological samples, biological samples and environmental samples comp)rising binding a compound of claim 1 or a conjugate of a compound of claim 1 to the metal cation and detecting, discriminating, or quantifying the metal cation bound compound or conjugate.

6. The method of claim 5 wherein the metal cation is involved in a biological process.

7. A method of detecting, discriminating, or quantifying processes occurring at surfaces comprising binding a compound of claim 1 or a conjugate of a compound of claim 1 to the metal cation on a surface and detecting, discriminating, or quantifying the metal cation bound compound or conjugate at the surface.

* * * * *

UNITED STATES PATENT AND TRADEMARK OFFICE
CERTIFICATE OF CORRECTION

PATENT NO. : 7,629,379 B2 Page 1 of 1
APPLICATION NO. : 10/557073
DATED : December 8, 2009
INVENTOR(S) : Wilson et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 356 days Delete the phrase "by 356 days" and insert -- by 590 days --

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,629,379 B2 | Page 1 of 1 |
| APPLICATION NO. | : 10/557073 | |
| DATED | : December 8, 2009 | |
| INVENTOR(S) | : John Robert Howe Wilson et al. | |

It is certified that error appears in the above-identified patent and that said Letters Patent is hereby corrected as shown below:

Col. 22, line 6, please replace claim 3 with the following:

"A compound as claimed in claim 1 wherein:
X is O, S, or $NR^1$ where $R^1$ is a linear or branched $C_{1-10}$ alkyl;
R is hydrogen or a linear or branched $C_{1-10}$ alkyl;
B is a hydrogen or a linear or branched $C_{1-10}$ alkyl and
one or both of C and D is $OR^2$, $NR^3R^4$ where $R^2$, $R^3$, and $R^4$ are each independently hydrogen, a linear or branched $C_{1-10}$ alkyl, or an optionally complex metal ion $M^{n+}/n$ wherein n is an integer from 1 to 8, or a linear or branched $C_{1-10}$ alkyl $NR^5R^6$ chain where $R^5$ and $R^6$ are each independently hydrogen, a linear or branched $C_{1-10}$ alkyl."

Col. 22, line 21, please replace claim 5 with the following:

"A method of detecting, discriminating, or quantifying metal cations in a wide range of solvents, chemical and waste streams, physiological samples, biological samples and environmental samples comprising binding a compound of claim 1 or a conjugate of a compound of claim 1 to the metal cation and detecting, discriminating, or quantifying the metal cation bound compound or conjugate."

Signed and Sealed this
Sixteenth Day of August, 2011

David J. Kappos
*Director of the United States Patent and Trademark Office*